United States Patent [19]

Kitagawa et al.

[11] Patent Number: 4,961,435
[45] Date of Patent: Oct. 9, 1990

[54] HIGH-FREQUENCY CAPACITIVE HEATING ELECTRODE DEVICE

[75] Inventors: Kiyoshi Kitagawa, Chiba; Yoshio Hosoi, Sendai; Akira Sogawa; Chikau Onodera, both of Tokyo; Tadashi Onuma, Inashiki, all of Japan

[73] Assignee: Kureha Kagaku Kogyo Kabushiki Kaishi, Tokyo, Japan

[21] Appl. No.: 258,513

[22] Filed: Oct. 17, 1988

[30] Foreign Application Priority Data

Oct. 28, 1987 [JP] Japan .................. 62-165167[U]

[51] Int. Cl.⁵ .............................................. A61N 5/00
[52] U.S. Cl. .................................. 128/788; 128/400; 128/401; 128/804
[58] Field of Search ............... 128/784, 788, 804, 400, 128/401

[56] References Cited

U.S. PATENT DOCUMENTS

| 4,140,130 | 2/1979 | Storm, III ..................... 128/804 |
| 4,676,258 | 6/1987 | Inokuchi et al. .............. 128/804 |

FOREIGN PATENT DOCUMENTS

| 0115420 | 8/1984 | European Pat. Off. . |
| 0139433B1 | 5/1985 | European Pat. Off. . |
| 0251745A1 | 1/1988 | European Pat. Off. . |
| 0251746A1 | 1/1988 | European Pat. Off. . |
| 0253677A1 | 1/1988 | European Pat. Off. . |
| 936281 | 12/1955 | Fed. Rep. of Germany . |
| 2407559 | 8/1975 | Fed. Rep. of Germany . |
| 205162 | 9/1959 | Netherlands . |
| 222800 | 8/1962 | Netherlands . |
| 234367 | 4/1986 | Netherlands . |
| 1093347 | 5/1984 | U.S.S.R. ....................... 128/784 |

*Primary Examiner*—Lee S. Cohen
*Attorney, Agent, or Firm*—Nixon & Vanderhye

[57] ABSTRACT

A high-frequency capacitive heating electrode device comprises a cap-shaped electrode, a flexible support for supporting the electrode with one end thereof capped with the electrode, a flexible polymer film which surrounds the electrode and forms a gastight space between the support and the flexible polymer film, and passages for respectively introducing and discharging a cooling medium to and from the gastight space. The high-frequency capacitive heating electrode device is disposed in the vicinity of the target portion of a living body to be heated and is useful for the hyperthermia therapy for a cancer of the uterine cervix.

13 Claims, 4 Drawing Sheets

Fig. 3a 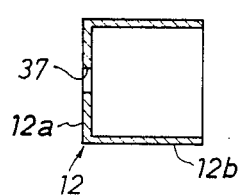 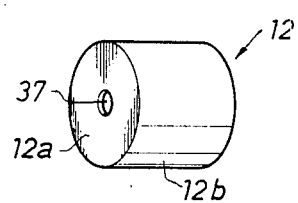 Fig. 3b
Fig. 3c 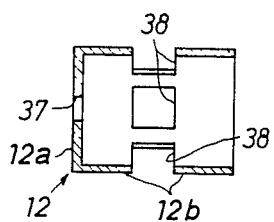 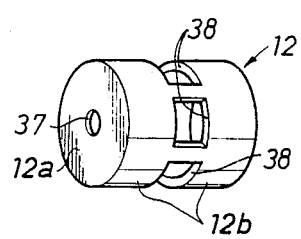 Fig. 3d
Fig. 3e 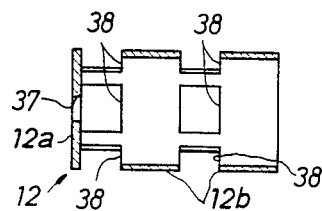 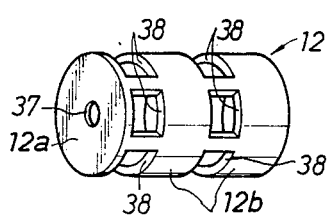 Fig. 3f
Fig. 3g 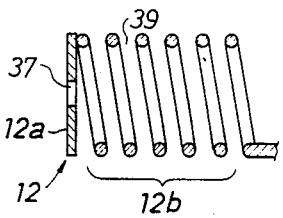 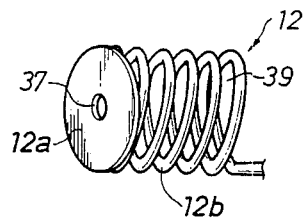 Fig. 3h
Fig. 3i 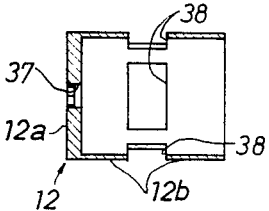 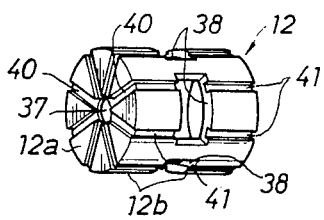 Fig. j

HIGH-FREQUENCY CAPACITIVE HEATING ELECTRODE DEVICE

BACKGROUND OF THE INVENTION

The present invention relates to a medical heating electrode device and, more particularly, to a high-frequency capacitive heating electrode device which is applicable to the hyperthermia therapy for tumors and the like.

There is known a high-frequency hyperthermia therapy for treating a cancer by utilizing the fact that cancer cells are less resistant to heat than normal cells.

In a conventional high-frequency capacitive hyperthermia therapy, the area of a living body including a portion to be heated is situated between two plate electrodes and a high-frequency current is supplied between the electrodes from a high-frequency power source.

It is difficult, however, to effectively heat the target portion at the deep inside of a living body by such a conventional treatment, because the subcutaneous fat layer tends to be heated more intensively so that this treatment gives pain to the patient.

To overcome such a problem, a method has been proposed in which a high-frequency current is applied between a first electrode which has a device for circulating a cooling medium and can be applied to the vicinity of the lesional portion at the deep inside of a living body and a second electrode which has a larger electrode area than the first electrode so that only the vicinity of the first electrode may be heated and is applied to the surface of the living body.

For example, Japanese Utility Model Application Laid-Open (KOKAI) Nos. 63-3844 (1988) and 63-3845 (1988) (corresponding to European Patent Application Laid-Open No. 0251746 A1) discloses a high-frequency capacitive heating electrode device which is applicable to the surface of an endotract organ.

The electrode device disclosed in Japanese Utility Model Application Laid-Open (KOKAI) No. 63-3845 (1988) is a high-frequency heating electrode device which comprises a thick-walled container of a flexible polymer which is equipped with passages for respectively introducing and discharging a cooling medium, an electrode easy to transform and disposed on the inner surface opposite to the open surface of the thick-walled container, and a flexible polymer film for sealing the open surface of the thick-walled container. This electrode device transforms in conformity with the configuration of the surface of the body (the outer surface of a living body and the surface of an endotract organ) and allows the desired portion in the vicinity of the electrode device to be selectively and reliably heated. Since the electrode does not come into close contact with the surface of the body, the electrode device is safe.

The electrode device disclosed in Japanese Utility Model Application Laid-Open (KOKAI) No. 63-3844 (1988) is a heating electrode device which comprises the high-frequency heating electrode device disclosed in Japanese Patent Application Laid-Open (KOKAI) No. 63-3845 (1988) and a gastight bag-like member disposed on the back surface of the thick-walled container of the high-frequency heating electrode device and having a function of introducing and discharging a gas, so that the electrode device is secured to the target lesional portion on the inner surface of an endotract organ (e.g., the inner surface of the vagina) without the necessity for separately preparing an electrode fixing device.

A high-frequency capacitive heating electrode device according to the present invention has been so devised as to be applicable to the treatment for a cancer of the uterine cervix, which is the surface of the endotract organ, and for the cancer which has infiltrated into the peripheral portion of the uterine cervix.

SUMMARY OF THE INVENTION

It is an object of the present invention to provide a high-frequency capacitive heating electrode device which is applicable to the treatment for a cancer of the uterine cervix, more preferably, which is capable of heating a wide area containing not only the uterine cervix but also the infiltrated area even if cancer of the uterine cervix is in an advanced stage and infiltrates in a wide region.

According to the present invention, this object is achieved by a high-frequency capacitive heating electrode device comprising an electrode, a flexible support for supporting the electrode, a flexible polymer film which surrounds the electrode and forms a gastight space between the support and the flexible polymer film, and passage means for introducing and discharging a cooling medium to and from the gastight space, the electrode being formed into a cap-like shape and disposed at one end of the flexible support.

Since the electrode of the high-frequency capacitive heating electrode device of the present invention has a cap-like shape, it is possible to simultaneously heat the portion of a living body which faces to the outer circumferential surface of the tubular portion of the cap-shaped electrode and the portion of the living body which faces to the plate-like portion disposed at the end of the tubular portion of the cap-shaped electrode. As the electrode of the electrode device which is used for the treatment for the cancer of the uterine cervix, the tubular portion of the cap-shaped electrode is, for example, cylindrical, and the plate-like portion of the electrode is, for example, discal. Accordingly, the electrode device is capable of heating a wide area containing not only the uterine cervix but also the infiltrated area even if the cancer of the uterine cervix is in an advanced stage and infiltrates in a wide region. The electrode device according to the present invention is easy to dispose at the portion to be heated, thereby enabling thermal treatment without any trouble.

The above and other objects, features and advantages of the present invention will become clear from the following description of the preferred embodiments thereof, taken in conjunction with the accompanying drawings.

BRIEF DESCRIPTION OF THE DRAWINGS

FIGS. 3a to 3j show the side cross sectional and perspective views of each of five alternative electrodes of embodiments in accordance with the invention;

DESCRIPTION OF THE PREFERRED EMBODIMENTS

Embodiments of the present invention will be explained with reference to the accompanying drawings.

Figure 1:
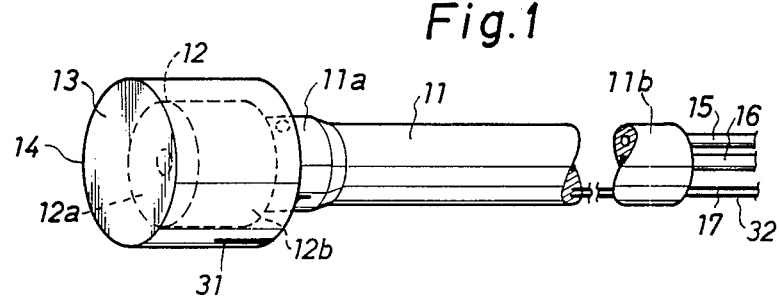
FIG. 1 is an explanatory view of an embodiment of an electrode device according to the present invention.

FIG. 1 is an explanatory view of an embodiment of a high-frequency capacitive heating electrode device according to the present invention. The reference numeral 11 denotes a support for supporting a cap-shaped electrode 12. The support 11 is provided with a lead wire 17 for supplying electricity to the cap-shaped electrode 12, passages 15 and 16 for introducing and discharging a cooling medium and a lead wire 32 for a sensor 31. The support 11 is made of a material which is easy to deform (bend) and has a hardness sufficient for retaining its shape. For example, the material may be a combination of a flexible polymer material and a metal such as a copper bar (not shown) in order to correctly dispose the cap-shaped electrode 12 at the portion to which it is to be applied. The shape and the size of the support 11 may be designed as desired in accordance with the purpose of use. For example, the support 11 may be cylindrical.

The support 11 shown in FIGS. 1 and 2a to 2c has a cylindrical rear half portion 11b having a smaller diameter than the forward half portion 11a. Alternatively, the rear half portion 11b of the support may have the same diameter as or a larger diameter than the forward half portion 11a depending upon the size of electrodes 12a and 12b. The forward half portion 11a is capped with the cap-shaped electrode 12 which comprises the discal electrode 12a facing to one end surface 35 of the support 11, and the cylindrical electrode 12b surrounding a part of the outer circumferential surface of the support 11 which extends from the peripheral edge of the end surface 35. The electrodes 12a and 12b are made of a good electrical conductor such as copper and silver and have a shape of, for example, a plate, foil, net and coil. The shape of the electrodes 12a and 12b are not necessarily dependent on the external form of the support 11. The electrodes 12a and 12b may be either integral or separate. The dimensions of the cap-shaped electrode 12 may be properly determined as required. In the case of an electrode device for the uterine cervix, the dimensions of the cap-shaped electrode 12 are, for example, about 1.5 to 3 cm in diameter and about 1.5 to 3.5 cm in length.

The lead wire 17 for connecting the electrodes 12a and 12b with a power source (not shown) passes through the support 11 and is connected to the electrodes 12a and 12b. A flexible polymer film 14 is provided on the side of the forward half portion 11a of the support in such a manner as to surround the electrodes 12a and 12b and form a gastight space 13 between the support 11 and the flexible polymer film 14. The shape of the flexible polymer film 14 is selected as desired in accordance with the portion to which the electrode device of the present invention is to be applied. The flexible polymer film 14 may be formed in advance such that the electrode device naturally comes into close contact with the portion to which the electrode device is to be applied. In this case, the cap-shaped electrode 12 preferably has an external shape approximate to the external shape of the flexible polymer film 14 so that a uniform current density is produced on the surface of the flexible polymer film 14. A groove may be provided on the surface of the electrode so as to secure the circulation passage for the cooling medium.

The gastight space 13 between the support 11 and the flexible polymer film 14 is filled with a cooling medium such as water and a conductive liquid so as to be circulated in the gastight space 13 through the introducing and discharging passages 15 and 16 provided on the support 11.

The flexible polymer film 14 facilitates the close contact between the electrode device and the target portion to be treated in association with the cooling medium to be circulated in the gastight space 13 in the case where the electrode device is disposed within a living body for the treatment.

The cooling medium is circulated in the gastight space 13 for the purpose of preventing local heating during the hyperthermia treatment.

Figure 2A:
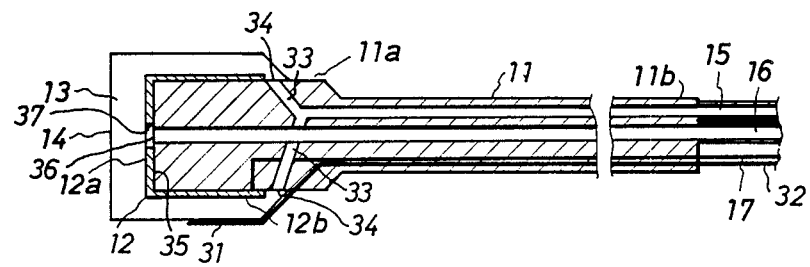
FIGS. 2a to 2c are sectional views of embodiments of an electrode device of the present invention.

The flexible polymer film 14 for effectively achieving the purpose of use of the cooling medium is exemplified by a polymer film made of a natural or synthetic rubber, for example, a silicone rubber film. FIGS. 1 and 2a show the electrode device provided with the sensor 31 connected to the lead wire 32 for the purpose of monitoring the heating state during the hyperthermia treatment, but in the case of preparing a temperature sensor separately, it is not necessary to provide the temperature sensor 31 and the lead wire 32 on the electrode device.

The cooling medium which is charged into and circulated in the gastight space 13 absorbs a part of the applied high-frequency energy. In order to reduce the energy absorption, the distance between the cap-shaped electrode 12 and the flexible polymer film 14 is appropriately selected depending upon the area of the cap-shaped electrode 12.

Figure 2B:
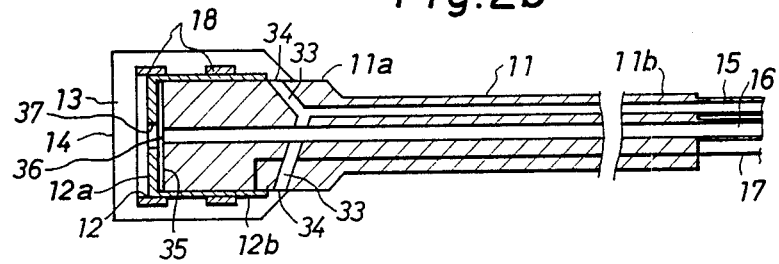
Figure 2C:
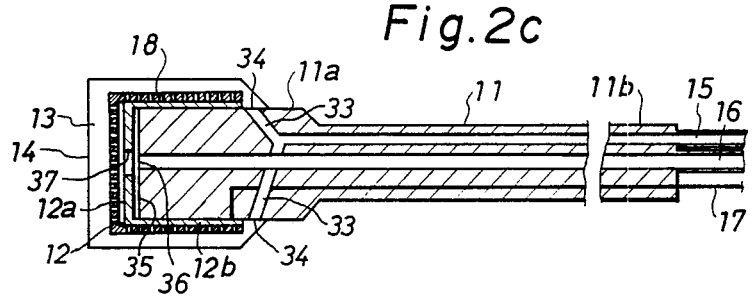

As shown in FIGS. 2a to 2c, the support 11 is pierced with the passages 15 and 16 for respectively introducing and discharging the cooling medium. It is also possible to use the passage 15 for discharging the cooling medium and the passage 16 for introducing the cooling medium. The passage 15 communicates with the gastight space 13 through an opening 34 provided on the outer circumferential surface of the forward half portion 11a of the support 11. One end of the passage 16 communicated with the gastight space 13 through an opening 36 provided on one end surface 35 of the support 11. The passages 15 and 16 may have branch passages which branch off from intermediate portion of each of the passages 15 and 16 and are respectively communicated with the gastight space 13 through a plurality of openings provided on the end surface 35 and the outer circumferential surface of the forward half portion 11a so as to correspond to the respective branch passages. The discal electrode 12a is pierced with a through hole 37 at the portion of the discal electrode 12a facing to the opening 36.

FIGS. 2a to 2c are section views of embodiments of an electrode device according to the present invention.

The electrode device shown in FIG. 2b is provided with ring spacers 18 of a silicone rubber or the like on the surface of the electrode. In the electrode device shown in FIG. 2c, the electrode is provided on the surface thereof with a spacer 18 which is formed of a reticulate, porous, or other polymeric material, for example, a cap-shaped reticulate spacer which is formed of polytetrafluoroethylene in conformity with the shape of the electrode. These spacers 18 prevent the electrodes 12a and 12b from coming into close contact with the flexible polymer film 14. If the thickness of the spacer is approximate to the distance between the cap-shaped electrode 12 and the flexible polymer film 14, it is possible to maintain a predetermined distance between the cap-shaped electrode 12 and the flexible polymer film 14 even if a local external pressure is applied to the electrode device during the hyperthermia treatment, whereby the omnipresence of the distance between the cap-shaped electrode 12 and the polymer film 14 in the respective portions of the cap-shaped electrode 12 is suppressed to thereby enable effective heating. The spacer 18 is fixed to the electrodes 12a and 12b in such a manner as to, for example, cap the electrodes 12a and 12 b.

FIGS. 3a to 3e show various examples of the structure of the cap-shaped electrode. FIGS. 3a to 3c show cap-shaped electrodes made of a plate, foil, or net of a good conductor metal such as copper. FIG. 3d shows a cap-shaped electrode in which the electrode 12b is formed in the shape of coil.

In the electrodes shown in FIGS. 3b to 3e, the electrode 12b is provided with apertures. These apertures are useful for suppressing the local flow of the cooling medium when a local external pressure is applied to the electrode device during the use for the hyperthermia treatment and the space between the cap-shaped electrode 12 and the flexible polymer film 14 is reduced or enlarged. In the case of the electrodes shown in FIGS. 3b and 3c, as the apertures provided on the electrode 12b, a plurality of rectangular openings 38 are provided at the outer circumferential portion of the electrode 12b at regular intervals. In the case of the electrode shown in FIG. 3d, the apertures are formed as a continuous space 39 defined by the coiled good conductor member. In the case of the electrode shown in FIG. 3e, apertures are provided in both the electrodes 12a and 12b. The apertures consist of a plurality of grooves 40 which are provided on the surface of the electrode 12a in such a manner as to extend radially from the through hole 37 to the outer periphery of the electrode 12a, a plurality of grooves 41 which are provided on the surface of the electrode 12b in such a manner as to extend from one end of the electrode to the other end and communicate to the corresponding grooves 40, and a plurality of rectangular openings 38 provided on the outer circumferential portion of the electrode 12d at regular intervals. The grooves 40 and 41 secure the circulation passages for the cooling medium and enhance the operation of the plurality of openings 38 for suppressing the local flow of the cooling medium.

The discal electrode 12a is disposed opposite to the end surface 35 of the support 11 in such a manner as to be perpendicular to the longitudinal axis of the support 11. The cap-shaped electrode 12 is fixed to the support 11 in such a manner as to cap the end portion of the support 11 on the side of the end surface 35 or adhered to the outer circumferential surface of the support 11 extending from the peripheral edge of the end surface 35 of the support 11.

The example of usage of an electrode device of the present invention will now be explained.

The electrode device of the present invention is inserted into the vagina and the support 11 is appropriately bent, if necessary, such that the electrode 12a is situated at the uterine cervix which is the target portion to be heated. In this state, the support 11 is fixed by a separately prepared means.

The cooling medium is next introduced to the space 13 through the introducing and discharging passages 15 and 16. As described above, the electrode device of the present invention which is disposed at the target portion to be heated an carry out high-frequency capacitive heating in combination with the electrode device disposed on the surface of the body. In this case, the use of an electrode device having an electrode area more than 10 times larger than that of the electrode device of the present invention as the external electrode device makes it possible to effectively treat the target portion to be heated at which the electrode device of the present invention is located.

The advantages obtained by the electrode device of the present invention will be described hereinunder.

Figure 4:
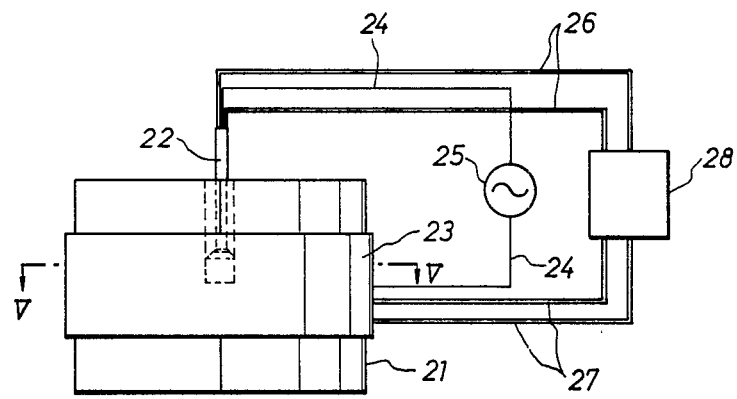
FIG. 4 is a schematic view of an experimental apparatus for testing the effects of an electrode device according to the present invention.

FIG. 4 is a schematic view of an experimental apparatus for confirming the effects of the electrode device of the present invention. The apparatus is comprises a heating electrode device 22 which is inserted into a muscle equivalent agar phantom 21, an external electrode device 23 provided on the outer surface of the muscle equivalent agar phantom 21, a high-frequency power source 25 connected to these electrode devices 22 and 23 through a lead wire 24, and a cooling water circulator 28 connected to the electrode devices 22 and 23 through cooling water circulating pipes 26 and 27, respectively.

The muscle equivalent agar phantom 21 is a columnar body having an ellipse section of about 29 cm in major axis and 20 cm in minor axis from the top to the bottom and having a height of about 19 cm. The composition by weight of the agar phantom 21 was 4% of agar, 0.24% of NaCl, 0.1% of $NaN_3$ and 95.66% of distilled water.

Figure 5:
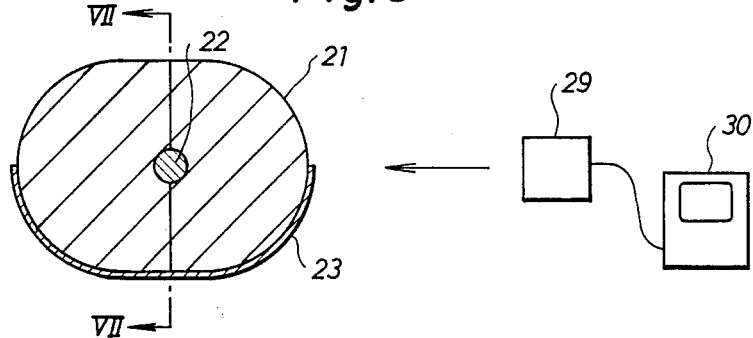
FIG. 5 is a sectional view of the apparatus shown in FIG. 4, taken along the line V—V and an explanatory view of a thermograph.

As the heating electrode device 22, the conventional electrode device disclosed in Japanese Utility Model Application Laid-Open (KOKAI) No. 63-3844 (1988) and the electrode device of the present invention were used. The muscle equivalent agar phantom 21 was heated by the two kinds of electrode devices and temperature distribution in the section of the agar phantom in each case taken along the line VII—VII was observed by a thermograph (infrared temperature measuring device) 29, 30 as shown in FIG. 5.

Figure 6A:
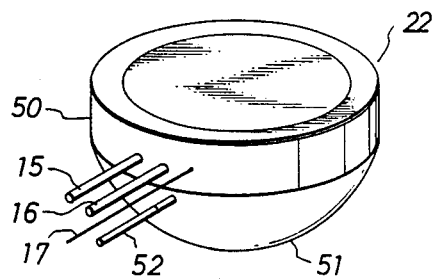
FIGS. 6a and 6b are explanatory views of a high-frequency heating electrode device in the prior art (disclosed in Japanese Utility Model Application Laid-Open (KOKAI) No. 63-3844 (1988))
Figure 6B:
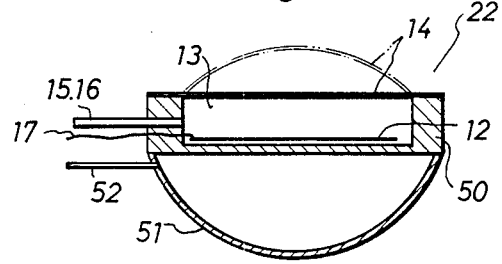

The electrode device of the present invention which was used in the experiment had a configuration shown in FIG. 2b and had a flexible polymer film 3 cm in diameter and 2.5 cm in length at the part of 3 cm in diameter. The conventional electrode device used in the comparative experiment had a configuration shown in FIG. 6a and 6b and the outer diameters of the ellipse were 5 cm×3 cm and the wall thickness was 1.4 cm. In FIGS. 6a and 6b, the reference numeral 12 denotes an electrode, 50 a thick-walled container, 51 a gastight bag member, and 52 a conduit.

Figure 7:
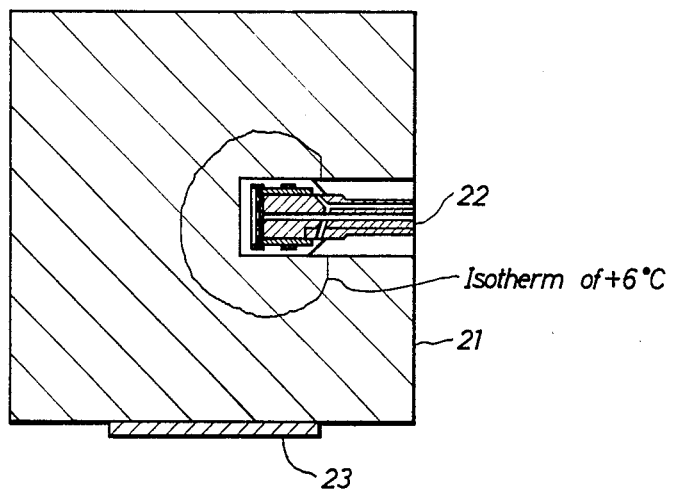
FIG. 7 is an isothermal chart which shows the results of the tests of the electrode device according to the present invention, which is obtained by the experimental apparatus shown in FIG. 4.

FIG. 7 shows the temperature distribution of the agar phantom which was heated by the electrode device of the present invention. The temperature distribution was shown as the isothermal chart representing the portions of the agar phantom which was higher by 6° C. than the temperature of the agar phantom before heating.

Figure 8:
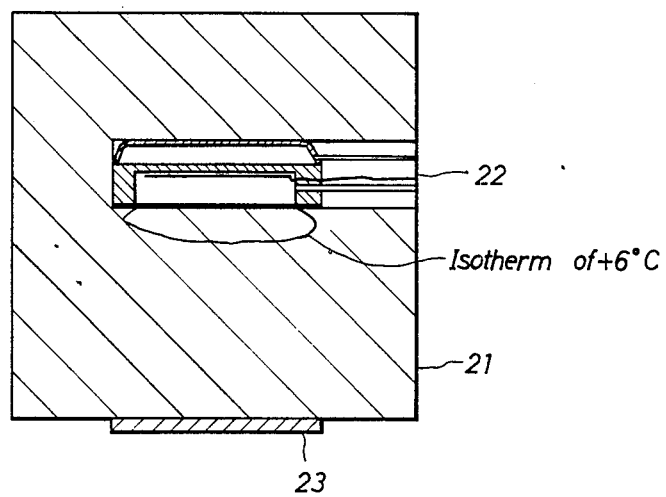
FIG. 8 is an isothermal chart which shows the results of the tests of a conventional electrode device, which is obtained by the experimental apparatus shown in FIG. 4.

FIG. 8 shows the temperature distribution of the agar phantom which was heated by the conventional electrode device. The temperature distribution was shown as the isothermal chart representing the portions of the agar phantom which was higher by 6° C. than the temperature of the agar phantom before heating.

Comparison of the isothermal chart in FIG. 7 with that in FIG. 8 clearly shows a difference in the patterns of the temperature distribution between the electrode device of the present invention and the conventional electrode device, which is not ascribed to the dimensional difference of the electrode devices. More specifically, since the high-frequency capacitive heating electrode device according to the present invention has a cap-shaped electrode, it is possible to simultaneously heat the part of a living body which is opposite to the outer circumferential surface of the cylindrical portion of the cap-shaped electrode and the part of a living body which is opposite to the discal portion of the cap-shaped electrode provided at the annular end of the cylindrical portion of the cap-shaped electrode. It is therefore possible to heat a wide area of the lesional portion containing not only the uterine cervix but also the infiltrated area even if the cancer of the uterine cervix is in an advanced stage and infiltrates in a wide region.

If a spacer is provided between the cap-shaped electrode and the flexible polymer film in order to prevent the close contact therebetween, as in the above-described embodiments, since the flexible polymer film does not come into close contact with the cap-shaped electrode, there is no extraordinary rise in the temperature of the portion at which the flexible polymer film comes into contact with the living body, and as a result the spacer enables safe hyperthermia treatment. The high-frequency capacitive heating electrode device according to the present invention is applicable to the hyperthermia treatment of other portions than the uterine cervix.

While there has been described what are at present considered to be preferred embodiments of the invention, it will be understood that various modifications may be made thereto and fall within the spirit and scope of the invention.

What is claimed is:

1. An intracavitary electrode device for a high-frequency capacitive heating device, comprising:
   a flexible member adapted to be inserted at a leading end portion thereof into an intracavity of an endotract organ of a living body;
   a cap-shaped electrode disposed around said leading end portion covering both of an end surface of said leading end portion and a circumferential surface of said leading end portion, said circumferential surface being adjacent to said end surface;
   a flexible polymer film enclosing said cap-shaped electrode so as to form a gas-tight space in association with said cap-shaped electrode and said flexible member, and secured on said flexible member at one end thereof;
   an introducing passage disposed in said flexible member for introducing a cooling medium into said gas-tight space; and
   a discharging passage disposed in said flexible member for discharging said cooling medium from said gas-tight space,
   each of said introducing passage and said discharging passage communicating with said gas-tight space.

2. An electrode device according to claim 1, wherein said flexible member is bendable and is capable of retaining a bent state.

3. An electrode device according to claim 2, wherein said cap-shaped electrode comprises a discal portion covering said end surface of said leading end portion, and a cylindrical portion connected to a circumferential portion of said discal portion at one end thereof, and surrounding said circumferential surface of said leading end portion.

4. An electrode device according to claim 1, wherein said cap-shaped electrode comprises as discal portion covering said end surface of said leading end portion, and a cylindrical portion connected to a circumferential portion of said discal portion at one end thereof, and surrounding said circumferential surface of said leading end portion.

5. An electrode device according to claim 4, wherein said discal portions provided with a through hole.

6. An electrode device according to claim 5, wherein said discal portion is provided on an outer surface thereof with a plurality of grooves extending from said through hole to said circumferential portion of said discal portion.

7. An electrode device according to claim 6, wherein said cylindrical portion is provided with a plurality of through holes formed at a wall portion of said cylindrical portion at regular intervals.

8. An electrode device according to claim 7, wherein said cylindrical portion is provided on an outer circumferential surface thereof with a plurality of grooves extending from respective portions of said cylindrical portion which correspond to terminals of a plurality of said grooves of said discal portion to the other end of said cylindrical portion which is opposite to said discal portion.

9. An electrode device according to claim 1, wherein a spacer for spacing said flexible polymer film from said cap-shaped electrode is disposed between said cap-shaped electrode and said flexible polymer film.

10. An electrode device according to claim 9, wherein said cap-shaped electrode comprises a discal portion covering said end surface of said leading end portion, and a cylindrical portion connected to a circumferential portion of said discal portion at one end thereof and surrounding said circumferential surface of said leading end portion, said spacer comprises a plurality of annular spacers, and one of said annular spacers which is arranged on a most leading end side of said cylindrical portion protrudes outwardly from said discal portion.

11. An electrode device according to claim 9, wherein said spacer is formed of a reticulate, porous or other material.

12. An electrode device according to claim 9, wherein said spacer is made of an insulating material.

13. An electrode device according to claim 12, wherein said insulating material is silicone rubber or fluorocarbon polymers.

* * * * *

UNITED STATES PATENT AND TRADEMARK OFFICE
CERTIFICATE OF CORRECTION

PATENT NO. : 4,961,435
DATED : October 9, 1990
INVENTOR(S) : Kitagawa et al

It is certified that error appears in the above-identified patent and that said Letters Patent is hereby corrected as shown below:

On the title page of the patent left hand column after

[73] Assignee:, please correct the spelling of the name of the Assignee to read:

--Kureha Kagaku Kogyo Kabushiki Kaisha--

Signed and Sealed this

Third Day of March, 1992

Attest:

HARRY F. MANBECK, JR.

*Attesting Officer*  *Commissioner of Patents and Trademarks*

UNITED STATES PATENT AND TRADEMARK OFFICE
CERTIFICATE OF CORRECTION

PATENT NO. : 4,961,435
DATED : October 9, 1990
INVENTOR(S) : Kiyoshi Kitagawa, et al It is certified that error appears in the above-identified patent and that said Letters Patent is hereby corrected as shown below:

Column 1, line 61, delete "Patent" and insert --Utility Model--.

Column 5, line 57, delete "12d" and insert --12b--.

Column 6, line 15, delete "an" and insert --can--.

In The Claims:

Column 8, Claim 4, line 2, delete "as" and insert --a--.

Signed and Sealed this

Thirty-first Day of March, 1992

Attest:

HARRY F. MANBECK, JR.

*Attesting Officer*     *Commissioner of Patents and Trademarks*